US011415792B2

(12) United States Patent
Chen

(10) Patent No.: US 11,415,792 B2
(45) Date of Patent: Aug. 16, 2022

(54) WIDE-ANGLE ENDOSCOPE LENS

(71) Applicant: ALTEK BIOTECHNOLOGY CORPORATION, Hsinchu (TW)

(72) Inventor: Chun-Yen Chen, Hsinchu (TW)

(73) Assignee: ALTEK BIOTECHNOLOGY CORPORATION, Hsinchu (TW)

( * ) Notice: Subject to any disclaimer, the term of this patent is extended or adjusted under 35 U.S.C. 154(b) by 707 days.

(21) Appl. No.: 16/454,069

(22) Filed: Jun. 27, 2019

(65) Prior Publication Data

US 2020/0004008 A1 Jan. 2, 2020

Related U.S. Application Data

(60) Provisional application No. 62/690,753, filed on Jun. 27, 2018.

(51) Int. Cl.
*G02B 23/24* (2006.01)
*H04N 5/232* (2006.01)
(Continued)

(52) U.S. Cl.
CPC ........ *G02B 23/243* (2013.01); *A61B 1/00183* (2013.01); *A61B 1/00195* (2013.01); *A61B 1/05* (2013.01); *G02B 13/04* (2013.01); *H04N 5/2254* (2013.01); *H04N 5/23238* (2013.01); *H04N 2005/2255* (2013.01)

(58) Field of Classification Search
USPC .......................................................... 359/749
See application file for complete search history.

(56) References Cited

U.S. PATENT DOCUMENTS 5,764,809 A * 6/1998 Nomami ................. G06T 11/00
382/209
2017/0199371 A1* 7/2017 Williamson ......... H04N 13/156

FOREIGN PATENT DOCUMENTS

| CN | 101681013 | 3/2010 | |
|---|---|---|---|
| CN | 104169775 | 11/2014 | |
| CN | 207473186 U | * 6/2018 | ............. G02B 13/00 |

OTHER PUBLICATIONS

Office Action of China Counterpart Application, dated Feb. 9, 2022, pp. 1-6.

* cited by examiner

*Primary Examiner* — Behrooz M Senfi
(74) *Attorney, Agent, or Firm* — JCIPRNET

(57) ABSTRACT

A wide-angle endoscope lens is configured to capture a large viewing angle area of a non-planar object to generate an image, wherein the wide-angle endoscope lens has a center region and a corner region. The center region has a corresponding central object distance range. The corner region surrounds and adjoins the center region, and has a corresponding corner object distance range, wherein the central object distance range is different from the corner object distance range, a first resolution of the image of the non-planar object captured at a central shortest object distance in the central object distance range and a second resolution of the image of the non-planar object captured at a central farthest object distance in the central object distance range are substantially the same, and a third resolution of the image of the non-planar object captured at a corner shortest object distance in the corner object distance range and a fourth resolution of the image of the non-planar object captured at a corner farthest object distance in the corner object distance range are substantially the same.

18 Claims, 13 Drawing Sheets

(51) Int. Cl.
*H04N 5/225* (2006.01)
*A61B 1/00* (2006.01)
*A61B 1/05* (2006.01)
*G02B 13/04* (2006.01)

| Embodiment 1 | | | | | |
|---|---|---|---|---|---|
| f= 0.431 mm, 0.7F Δ = -14 μm, Δ/f= 3.2%, FOV= 142 deg | | | | | |
| Element | Surface | Radius (mm) | Thickness (mm) | Refractive index | Abbe Number |
| Object | | Infinity | 10 | | |
| First lens | Object-side surface | 11 | 0.22 | 1.53116 | 56.044 |
| | Image-side surface | 0.541 | 0.342 | | |
| Second lens | Object-side surface | 3.877 | 0.813 | 1.642199 | 22.409 |
| | Image-side surface | 1.196 | 0.103 | | |
| Aperture | | Infinity | 0.011 | | |
| Third lens | Object-side surface | 0.571 | 0.22 | 1.491 | 57.2 |
| | Image-side surface | -1.151 | 0.103 | | |
| Fourth lens | Object-side surface | 0.607 | 0.22 | 1.5345 | 57.095 |
| | Image-side surface | 1.055 | 0.099 | | |
| Fifth lens | Object-side surface | 0.955 | 0.22 | 1.53116 | 56.044 |
| | Image-side surface | 1821.5 | 0.444 | | |
| | Image plane | Infinity | | | |

FIG. 10A

| Surface | | K | $a_2$ | $a_4$ | $a_6$ | $a_8$ | $a_{10}$ |
|---|---|---|---|---|---|---|---|
| First lens | Object-side surface | 0 | | | | | |
| | Image-side surface | 0 | 0.000 | -3.948 | 12.427 | 0.000 | 0.000 |
| Second lens | Object-side surface | 0 | 0.000 | 1.313 | 1.355 | 0.000 | 0.000 |
| | Image-side surface | 0 | 0.000 | 10.758 | -244.121 | 0.000 | 0.000 |
| Third lens | Object-side surface | 0 | 0.000 | -3.261 | 657.239 | 0.000 | 0.000 |
| | Image-side surface | 0 | 0.000 | -25.179 | 470.385 | 0.000 | 0.000 |
| Fourth lens | Object-side surface | 0 | 0.000 | -28.379 | 85.809 | 0.000 | 0.000 |
| | Image-side surface | 0 | 0.000 | -27.205 | 75.101 | 0.000 | 0.000 |
| Fifth lens | Object-side surface | 0 | 0.000 | -36.352 | 157.048 | 0.000 | 0.000 |
| | Image-side surface | 0 | 0.000 | -3.628 | 4.84 | 0.000 | 0.000 |

FIG. 10B

| Embodiment 2 | | | | | |
|---|---|---|---|---|---|
| f= 0.586 mm, 0.7F Δ = -16 μm, Δ/f= 2.7%, FOV= 140 deg | | | | | |
| Element | Surface | Radius (mm) | Thickness (mm) | Refractive index | Abbe Number |
| Object | | Infinity | 13.5 | | |
| First lens | Object-side surface | 15 | 0.299 | 1.53116 | 56.044 |
| | Image-side surface | 0.521 | 0.467 | | |
| Second lens | Object-side surface | 2.881 | 0.627 | 1.632809 | 23.336 |
| | Image-side surface | 1.335 | 0.14 | | |
| Aperture | | Infinity | 0.015 | | |
| Third lens | Object-side surface | 0.782 | 0.302 | 1.491 | 57.2 |
| | Image-side surface | -1.92 | 0.141 | | |
| Fourth lens | Object-side surface | 0.797 | 0.3 | 1.5345 | 57.095 |
| | Image-side surface | 1.062 | 0.135 | | |
| Fifth lens | Object-side surface | 0.663 | 0.298 | 1.525279 | 55.951 |
| | Image-side surface | Infinity | 0.439 | | |
| | Image plane | Infinity | | | |

FIG. 11A

| Surface | | K | $a_2$ | $a_4$ | $a_6$ | $a_8$ | $a_{10}$ |
|---|---|---|---|---|---|---|---|
| First lens | Object-side surface | 0 | | | | | |
| | Image-side surface | 0 | -0.424 | -1.615 | 4.082 | -5.379 | 0.000 |
| Second lens | Object-side surface | 0 | 0.122 | 1.279 | -2.650 | 7.401 | 0.000 |
| | Image-side surface | 0 | 0.307 | -14.622 | 511.419 | 0.000 | 0.000 |
| Third lens | Object-side surface | 0 | 0.002 | -8.603 | -215.700 | 0.000 | 0.000 |
| | Image-side surface | 0 | -0.274 | 3.380 | -421.659 | 0.000 | 0.000 |
| Fourth lens | Object-side surface | 0 | -0.560 | 3.567 | -236.400 | 1838.000 | 0.000 |
| | Image-side surface | 0 | -0.454 | -3.916 | -21.048 | 187.330 | 0.000 |
| Fifth lens | Object-side surface | 0 | 0.767 | -12.795 | 60.453 | -107.630 | 0.000 |
| | Image-side surface | 0 | 1.141 | -8.838 | 49.082 | -89.440 | 0.000 |

FIG. 11B

WIDE-ANGLE ENDOSCOPE LENS

CROSS-REFERENCE TO RELATED APPLICATION

This application claims the priority benefit of U.S. provisional application Ser. No. 62/690,753, filed on Jun. 27, 2018. The entirety of the above-mentioned patent application is hereby incorporated by reference herein and made a part of this specification.

BACKGROUND OF THE INVENTION

1. Field of the Invention

The present invention relates to an optical lens, in particular, to a wide-angle endoscope lens.

2. Description of Related Art

In general lens design, the optimal imaging positions of image center and corner are configured on a same image distance to the greatest extent. Thus, a balance may be reached at the imaging results of an object at the near point, the middle point and the far point, and the imaging resolution of the object at the near point and the far point is optimized. Such design is applicable to commercial, people's livelihood or industrial products, for example, application to digital cameras, phone cameras, sporting cameras, cameras for monitoring systems or cameras for automatic production.

Because object surface shoot by the cameras is approximately planar, or it is approximate the actual result by supposing that the surface is a plane, the lenses of the cameras are designed according to the foregoing method. However, in the field of endoscope, the object surface is variable, the condition of not approximating the plane frequently occurs, and therefore, a new endoscope needs a wide angle, namely, a large angle of field of view, besides expected great depth of field. With these requirements, even if the resolution quality of the center meets the requirement of depth of field, in the aspect of the resolution of the corner, only the resolution of the object in the middle point is relatively high, and can meet the requirement, however, the resolution of the object at the near point and the far point is low, resulting in the phenomenon that the resolution of the corner is insufficient, especially, the resolution of the object at the near point is often low.

SUMMARY OF THE INVENTION

The present invention provides a wide-angle endoscope lens, which is capable of solving the problem that the resolution of the corner is insufficient.

The wide-angle endoscope lens according to the present invention is configured to capture a large viewing angle area of a non-planar object to generate an image. The wide-angle endoscope lens has a center region and a corner region. The center region has a corresponding central object distance range. The corner region surrounds and adjoins the center region, and has a corresponding corner object distance range, the central object distance range is different from the corner object distance range, a first resolution of the image of the non-planar object captured at a central shortest object distance in the central object distance range and a second resolution of the image of the non-planar object captured at a central farthest object distance in the central object distance range are substantially the same, and a third resolution of the image of the non-planar object captured at a corner shortest object distance in the corner object distance range and a fourth resolution of the image of the non-planar object captured at a corner farthest object distance in the corner object distance range are substantially the same.

A wide-angle endoscope lens according to the present invention is configured to capture a large viewing angle area of a non-planar object to generate an image. The wide-angle endoscope lens has a center region and a corner region. The corner region surrounds and adjoins the center region, and a position of an image distance corresponding to a peak of a resolution curve in the corner region of the wide-angle endoscope lens shifts by a predetermined distance relative to a position of an image distance corresponding to a peak of a resolution curve in the center region.

Based on the abovementioned, in the wide-angle endoscope lens according to the present invention, the position of the image distance corresponding to the peak of the resolution curve in the corner region shifts by a predetermined distance relative to the position of the image distance corresponding to the peak of the resolution curve in the center region, so that greater resolution is achieved when imaging at both near object distance and far object distance, and the resolution of the corner region is effectively promoted while maintaining the resolution of the center region of the image.

In order to make the aforementioned and other objectives and advantages of the present invention comprehensible, embodiments are described in detail below with reference to the accompanying figures.

BRIEF DESCRIPTION OF THE DRAWINGS

FIG. 10A and FIG. 10B show optical datas of the wide-angle endoscope lens of an embodiment of the present invention.

FIG. 11A and FIG. 11B show optical datas of the wide-angle endoscope lens of another embodiment of the present invention.

DESCRIPTION OF THE EMBODIMENTS

According to the present invention, comparatively good design is performed according to relatively common object distance distribution phenomenon of the endoscope, and based on optimal center depth of field, the design of imaging position of corner depth of field is performed, so that the resolution in the range of depth of field is improved. That is, by setting the optimal imaging positions of the center and the corner, comparatively good image resolution at the near point, the middle point and the far point is realized.

Figure 1:
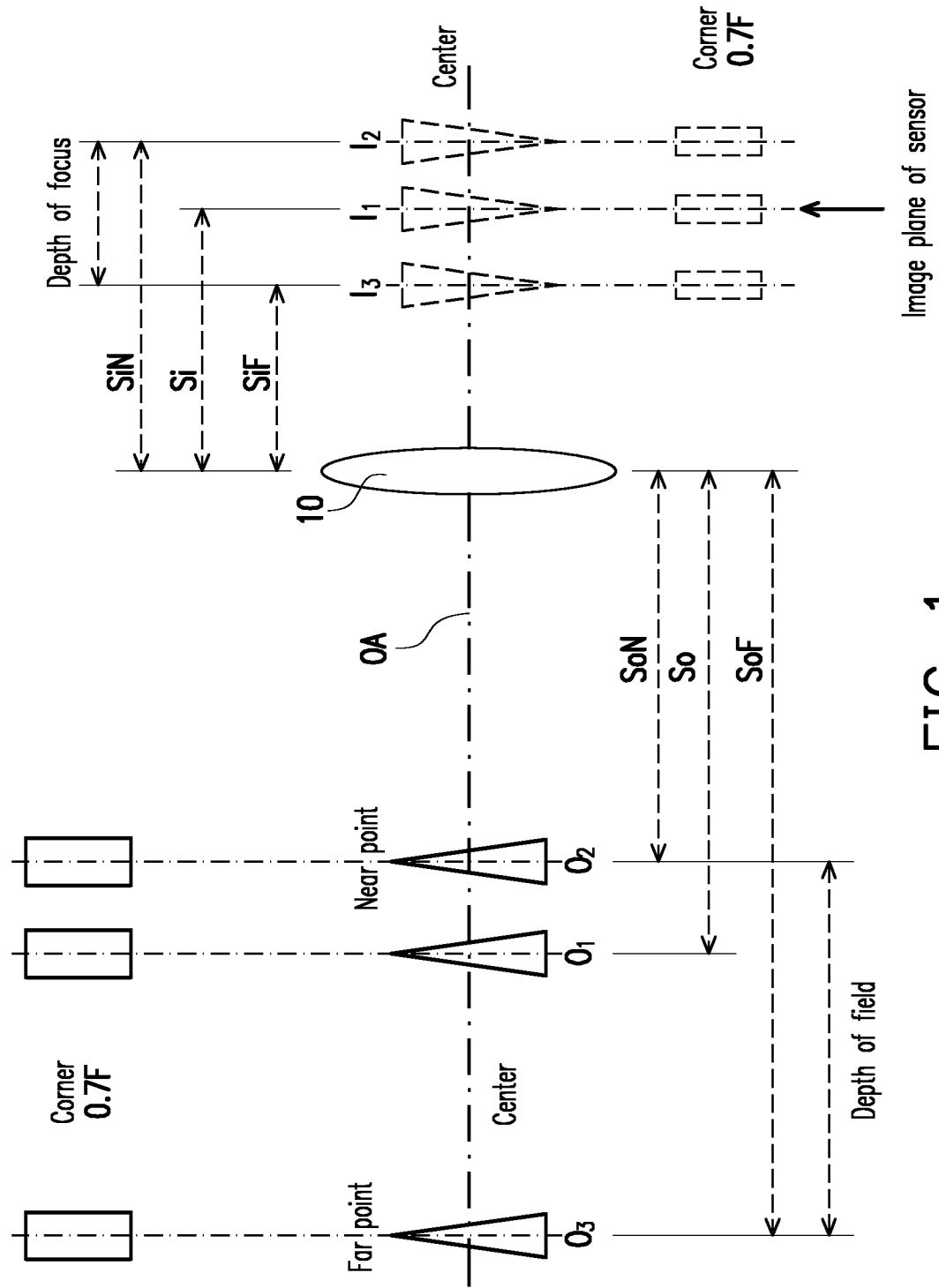
FIG. 1 shows a schematic diagram of an imaging principle of a lens.

FIG. 1 shows a schematic diagram of an imaging principle of a lens. Referring to FIG. 1, an object space is arranged at the left of a lens 10, an imaging space is arranged at the right, the lens 10 is located therebetween, an image sensor (called as film when being applied to a conventional camera) is placed in the imaging space, and the sensing plane thereof is on an image plane.

The objects in FIG. 1 are represented by solid lines. The objects located in the center region are represented by triangles, and the objects located at the corner region are represented by rectangles. Images in FIG. 1 are represented by dotted lines, images in the center region are represented by triangles, and images located at the corner region are represented by rectangles. In FIG. 1, the center region, for example, is an area close to the optical axis OA, and the corner region, for example, is an area with 0.7 field of view.

According to the imaging principle of geometrical optics, $1/So+1/Si=1/f$, where So is object distance, Si is image distance, and f is focal length. When the object (solid line) is located in the to-be-shot focusing middle position $O_1$ (object distance So), the image (dotted line) is imaged on the sensing plane of the image sensor, i.e., the imaging point $I_1$ (image distance Si). When the object (solid line) offsets rightwards near to the position $O_2$ (object distance SoN), the image (dotted line) also offsets rightwards to the imaging point $I_2$ (image distance SiN). When the object (solid line) offsets leftwards to the position $O_3$ (object distance SoF), the image (dotted line) also offsets leftwards to the imaging point $I_3$ (image distance SiF). When the object and the image move, the center regions and the corner regions thereof are on a same plane. Under the condition that the image resolution reaches the requirement, a distance between the farthest object distance SoF (Far Point) and nearest image distance SoN (Near Point) is called as depth of field (DOF), and a distance between the farthest image distance SiF (Far Point) and the nearest image distance SiN (Near Point) is called as depth of focus.

Figure 2:
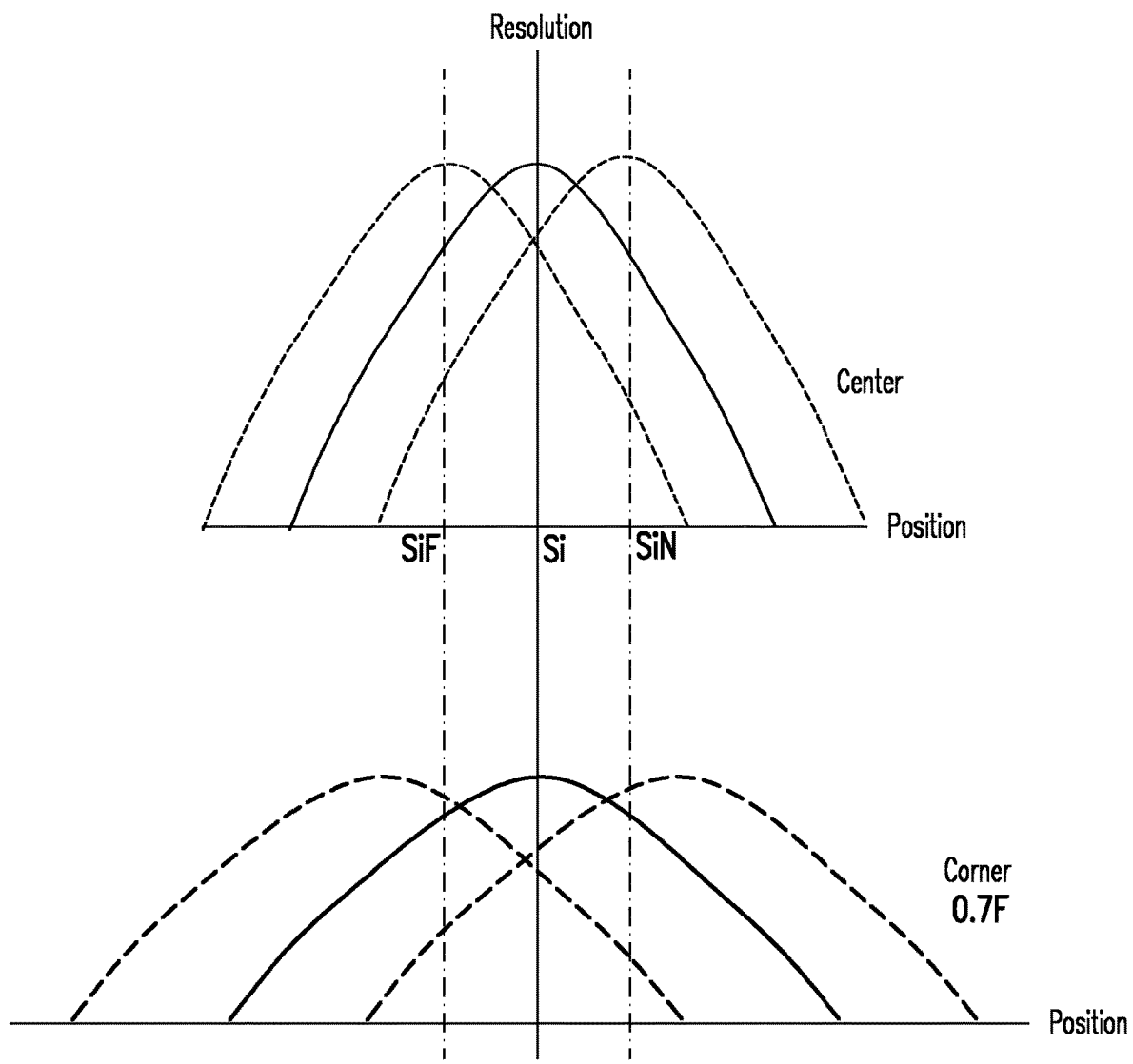
FIG. 2 shows a schematic diagram of an optimal imaging position of a general lens design.

FIG. 2 shows a schematic diagram of an optimal imaging position of a general lens design. A bell-shaped curve in the figure is a schematic diagram of a typical optical resolution curve, for example, through focus optical modulation transfer function (MTF). MTF may also be replaced with resolution curves with similar characteristics, for example, contrast, TVL, line pair or cycles which are all available optical resolution characteristic curves. The higher the numerical value, the better the resolution, and the peak of the curve is the optimal imaging point. Referring to FIG. 2, the horizontal axis represents position, the vertical axis represents the specific value of resolution or relative resolution, the curve in the upper side of the figure represents the MTF curve (or optical resolution characteristic curve) of the center region, the curve in the lower side of the figure represents the MTF curve (or the optical resolution characteristic curve) in the corner region, and the corner image is commonly represented by 0.7 field of view (0.7F). In FIG. 2, the solid line represents the resolution curve at the image distance Si, the dotted lines represent resolution curves at the image distance SiF and the image distance SiN, as shown in FIG. 2, with regard to the imaging point and depth of focus of FIG. 1, because the center and corner objects corresponding to the image center and corner regions are on a same plane, i.e., on the same object distance position, the optimal imaging positions of the image center and corner regions are on a same object distance position. Therefore, the peaks of the resolution curves of the image center and corner regions of the general lens design are designed on a same image distance to the greatest extent. The resolution curves move along with the image distance (for example image distance SiF or image distance SiN) which corresponds to distances of the objects (for example, object distance SoF or object distance SoN). As shown in the figure, under the condition that the image distances are respectively image distance SiF and image distance SiN, the values of the curves thereof on the sensing plane (for example, at the image distance Si) are approximate, so as to achieve the optimal design of the image resolution of at the near point, the middle point and the far point at the image center and corner regions. However, for the object surface that is not approximate to a plane, such design is not the optimal design.

Figure 3A:
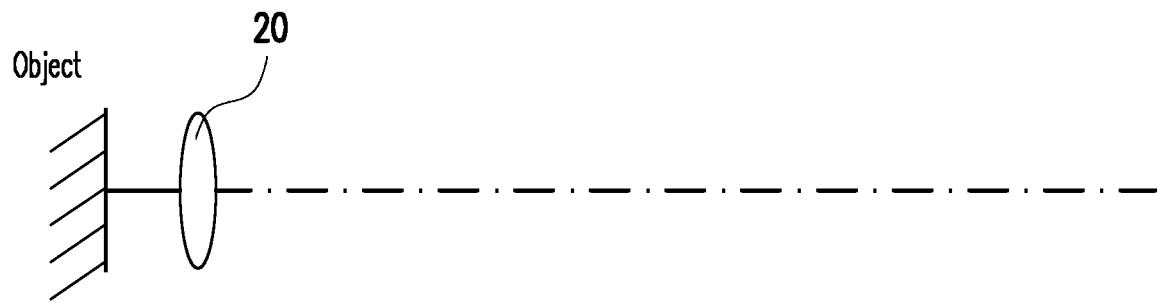
FIG. 3A to FIG. 3C show a design basis of an endoscope lens.
Figure 3B:
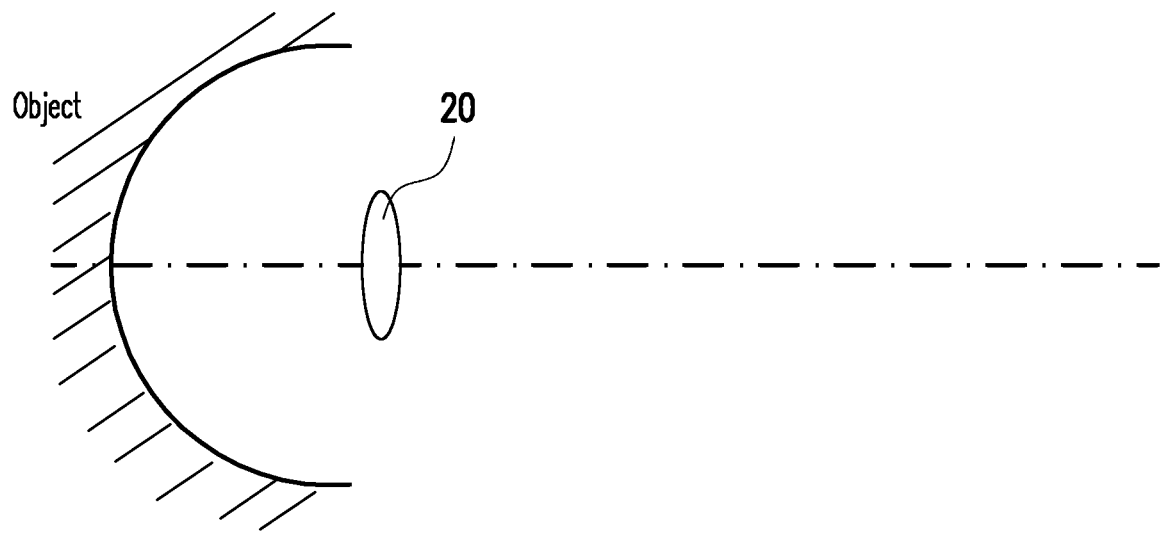
Figure 3C:
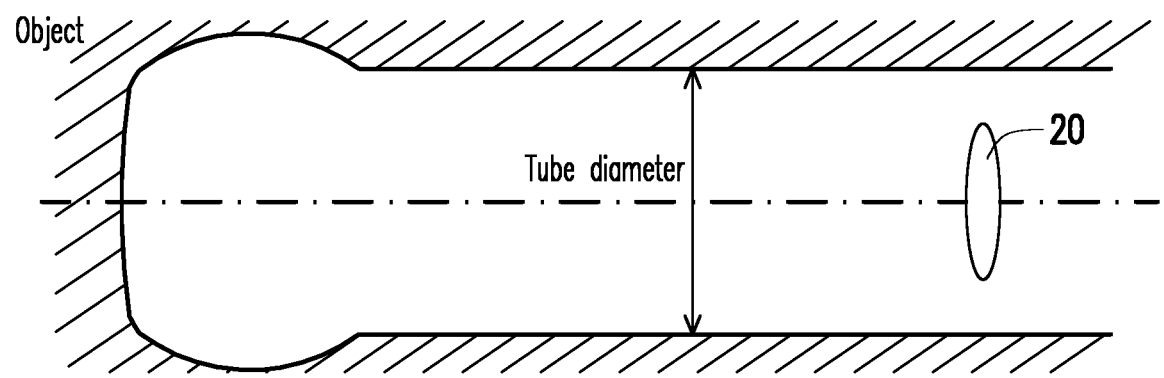

FIG. 3A to FIG. 3C show a design basis of an endoscope lens. A typical example is shown in FIG. 3A to FIG. 3C. The object represents a part which needs to be observed by the endoscope, and includes but is not limited to organs such as esophagus, stomach and large intestine. Of course, the part which needs to be observed by the endoscope is also not limited to the human body or animal, and the endoscope lens also may be utilized for parts which need to be observed by the endoscope in other industries, for example, used for intra-hole or pipeline detection and repair. The oval part represents a lens 20. As shown in FIG. 3A, when the object distance is relatively short, the object area observed by the lens 20 is relatively small, and is similar to a plane. As shown in FIG. 3B, when the object distance is slightly longer, the object area observed by the lens 20 is relatively large, and is similar to an arc-shaped curve. As shown in FIG. 3C, when the object distance is further longer, the object observed by the lens 20 is similar to a pipeline. The angle of field of view (FOV) of the wide-angle endoscope lens of the embodiment of the present invention is relatively large, for example, is larger than or equal to 110 degrees, and the lens is a lens with wide angle of view, and when the object distance of the image center changes, the variation of the object distance at the image corner is different from that of the image center.

Figure 4A:
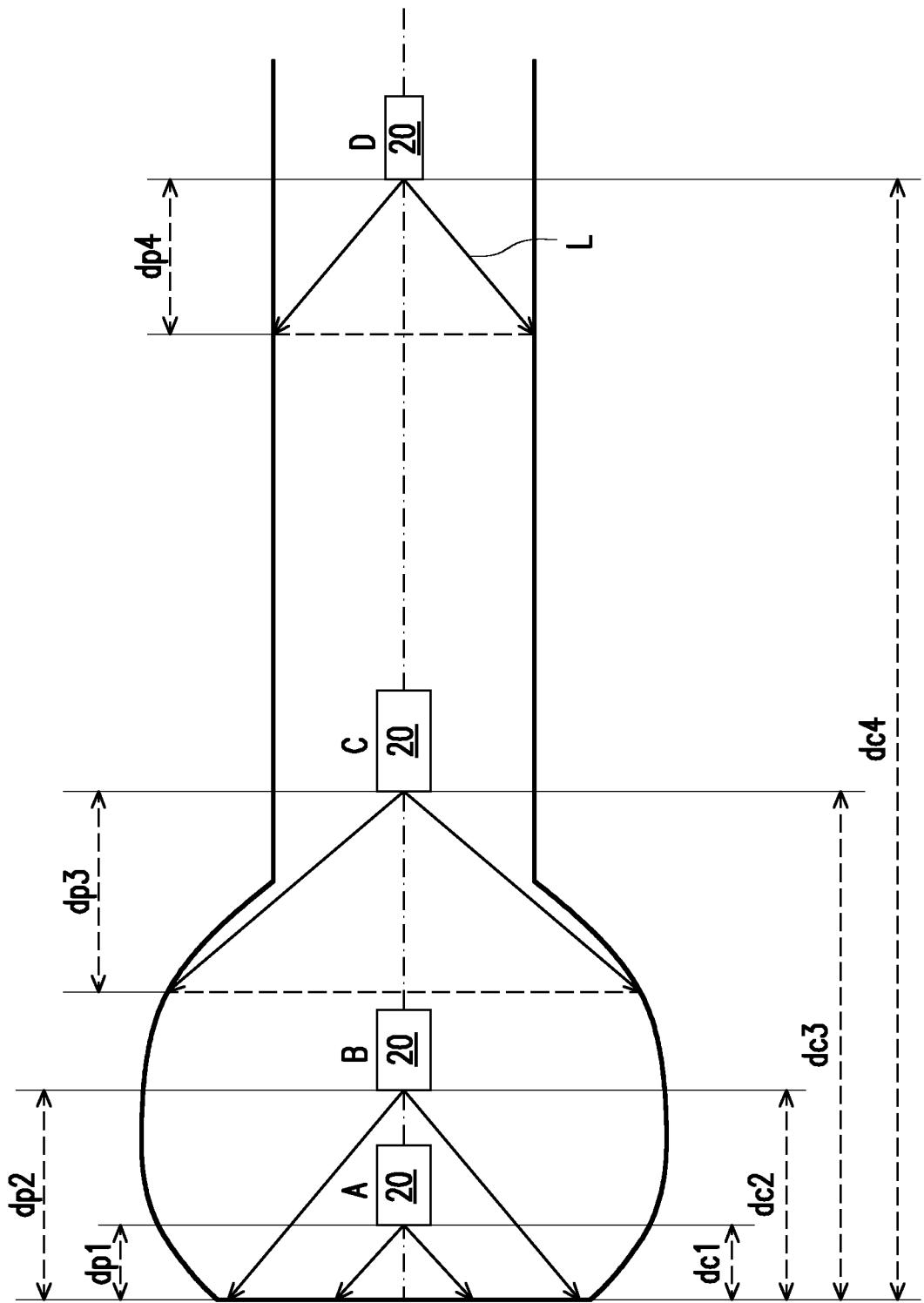
FIG. 4A shows an object environment of a typical endoscope camera described according to FIG. 3A to FIG. 3C.
Figure 4B:
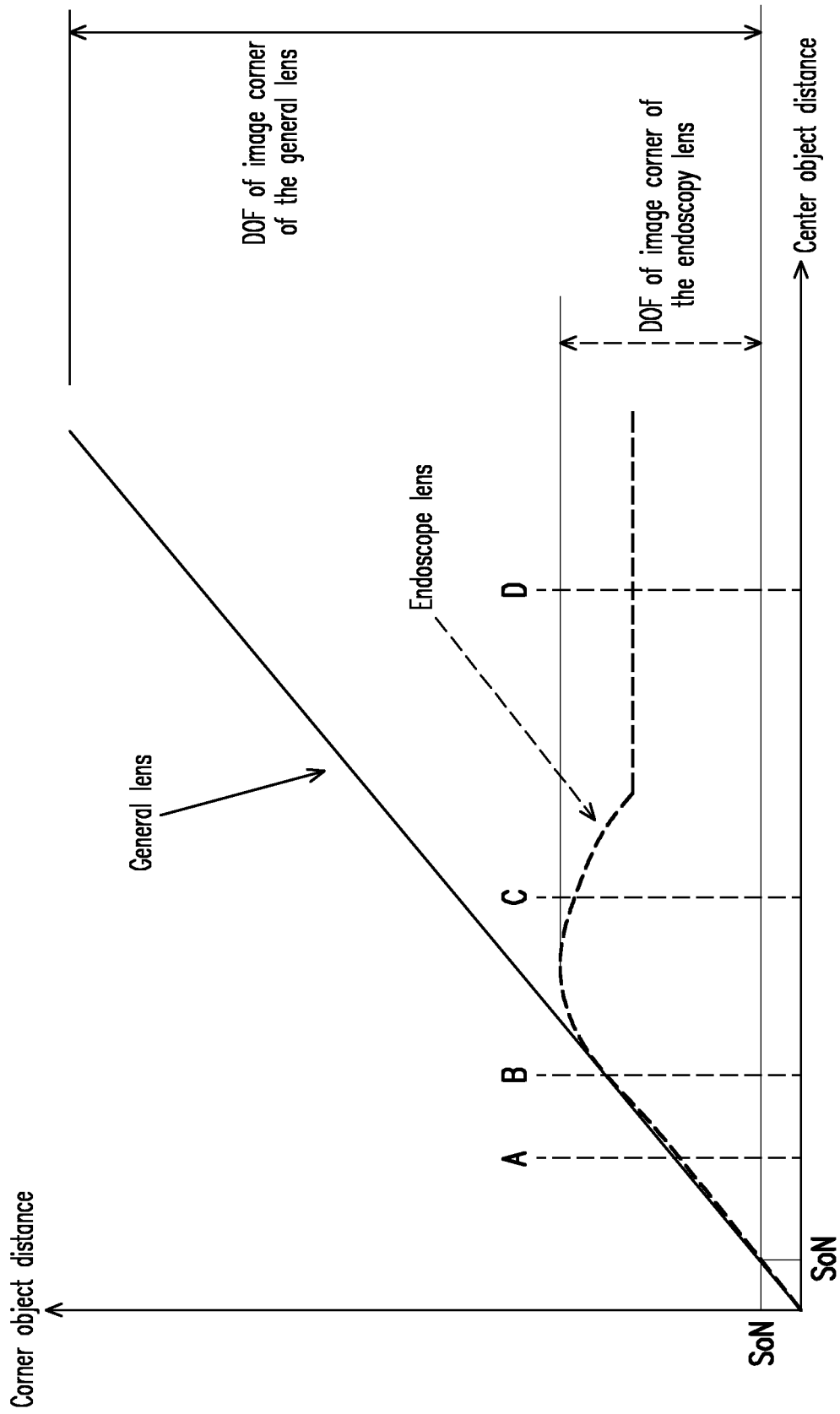
FIG. 4B shows a relation diagram between corner object distances and central object distances of a general lens design and a typical endoscope lens design.

FIG. 4A shows an object environment of a typical endoscope camera described according to FIG. 3A to FIG. 3C. FIG. 4B shows a relation diagram between corner object distances and central object distances of a general lens design and a typical endoscope lens design. In order to clearly express, in FIG. 4A, the space form in the object is shown by a relatively thick line in particular.

Referring to FIG. 4A first, an image corner beam L intersects with the object at an intersected position (the object point), and a distance that the image corner beam L projected onto the optical axis OA is the image corner object distance. For example, when the lens 20 is in the position A (for example, the near point), the image has a corner object distance dp1 and a center object distance dc1, and the corner object distance dp1 is equal to the center object distance dc1. When the lens 20 is in the position B (for example, the focal point), the image has a corner object distance dp2 and a center object distance dc2, and the corner object distance dp2 is equal to the center object distance dc2. When the lens 20 is in the position C (for example, the middle point), the image has a corner object distance dp3 and a center object distance dc3, and the corner object distance dp3 is smaller than the center object distance dc3. When the lens 20 is in the position D (for example, the far point), the image has a corner object distance dp4 and a center object distance dc4, and the corner object distance dp4 is smaller than the center object distance dc4. The near point, focal point, middle point or far point mentioned herein is with regard to the distance from the lens 20 to the object in front of the lens 20.

The relation between the image corner object distance and the image center object distance is approximately as shown in FIG. 4B. As shown in FIG. 4B, the solid line is the general lens design, and the center object distance and the corner object distance of the image thereof are the same. The dotted line is the design basis of the endoscope lens of the present invention, and the center object distance and the corner object distance of the image may be different (for example, position C and position D). Compared with the general lens design, DOF of the image corner region of the endoscope lens design of the present invention is much smaller obviously.

Figure 5A:
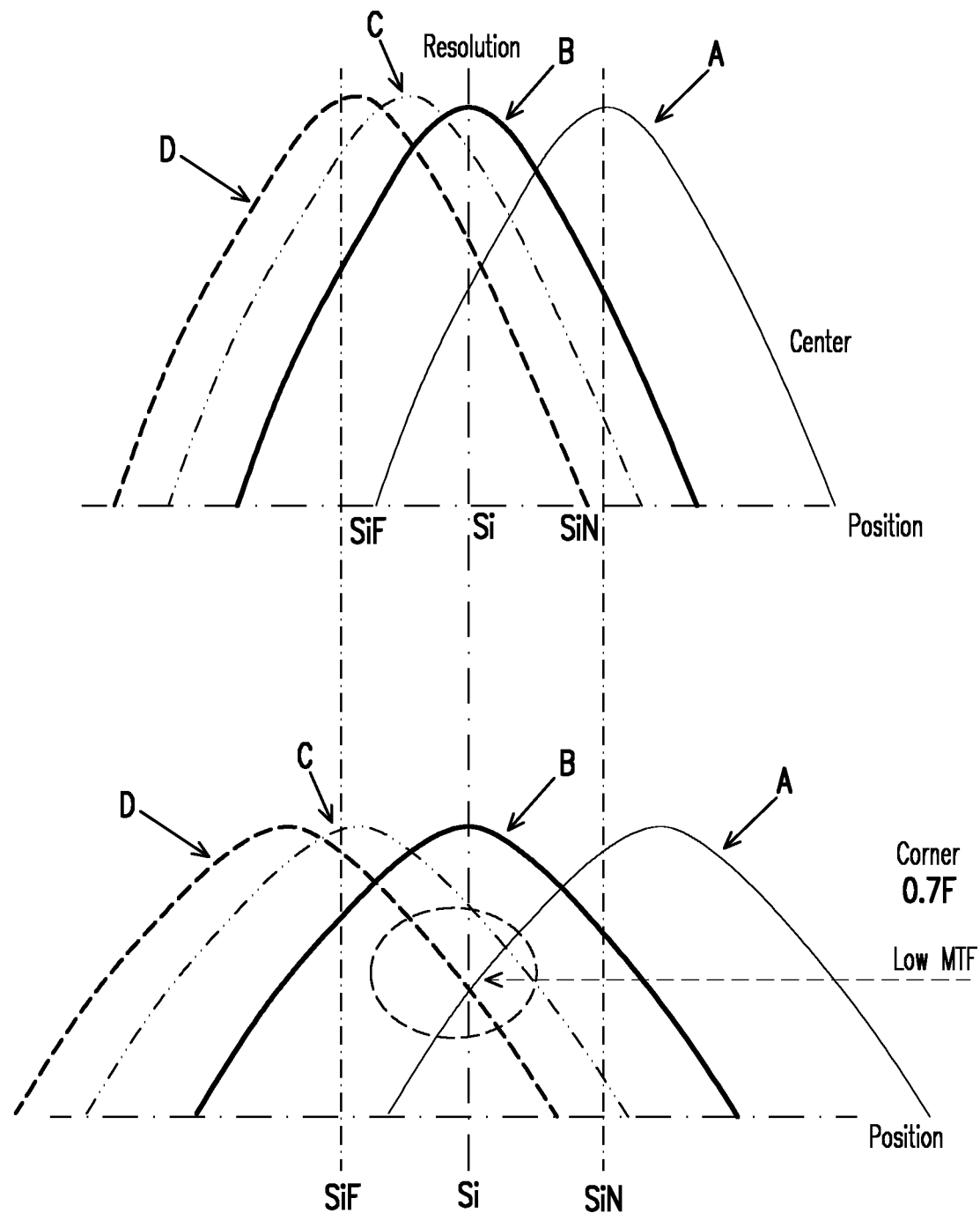
FIG. 5A and FIG. 5B show a schematic diagram taking a resolution MTF target of imaging as design reference.
Figure 5B:
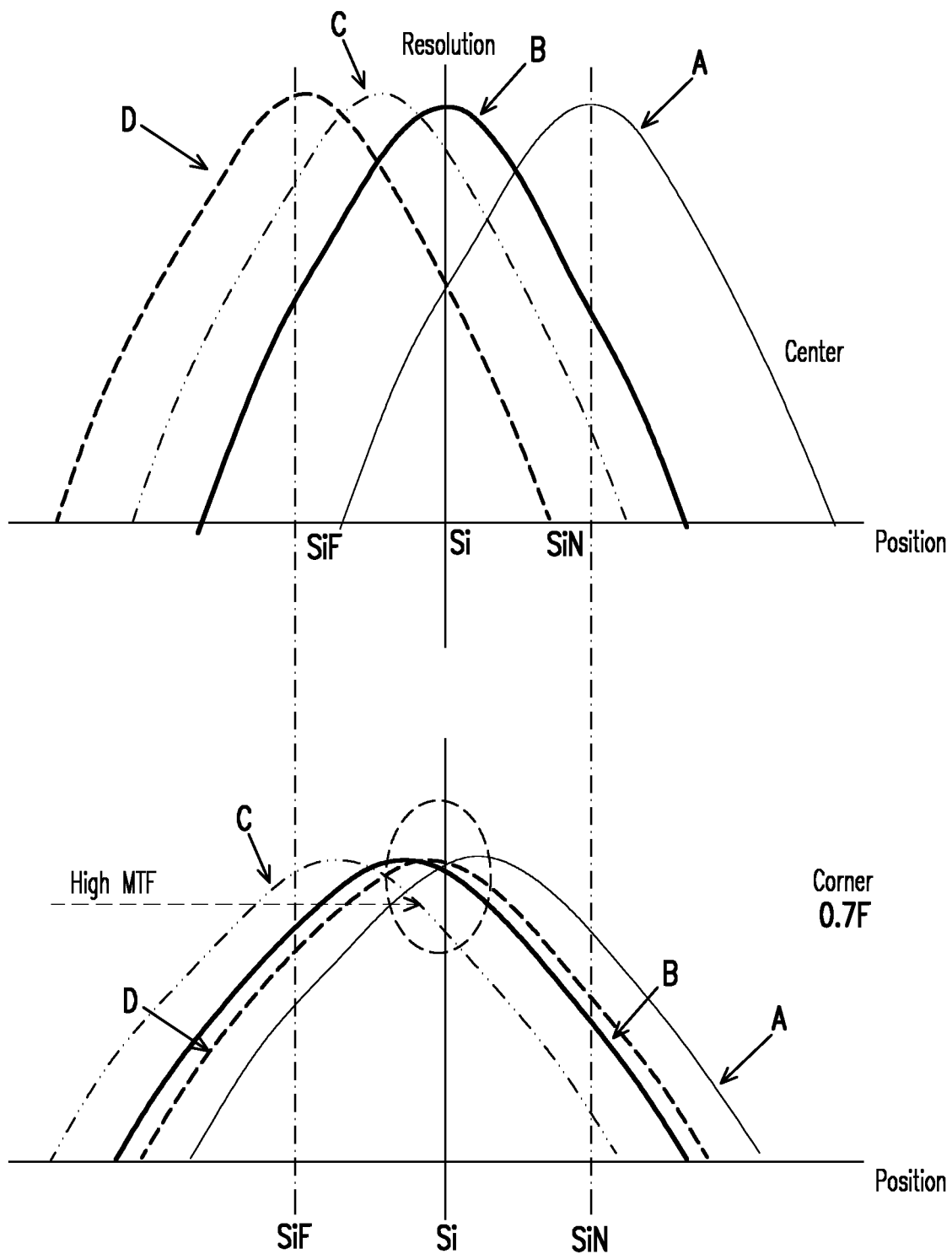

FIG. 5A and FIG. 5B show schematic diagrams taking a resolution MTF target of imaging as design reference, which corresponds to the state of FIG. 4A and FIG. 4B. The horizontal axis represents position, the vertical axis represents resolution or ratio of relative resolutions, the curve in the upper side of the figure represents the MTF curve (or optical resolution characteristic curve) in the center region, the curve in the lower side of the figure represents the MTF curve (or the optical resolution characteristic curve) in the corner region, and the corner image is commonly represented by using 0.7 field of view (0.7F). The solid line is the curve of imaging on the plane of the focal point, the dotted line is the MTF curve after movement of the image plane when the object distance changes, and curves corresponding to the position A to the position D in the FIG. 4A are respectively drawn in the figures. FIG. 5A is a conventional case that peaks of the center region and the corner region are on a same image distance (for example, image distance Si). The arrangement of the MTF curve of the present embodiment are different from conventional arrangement, as shown in FIG. 5B, with regard to the image corner DOF, the position of the peak of MTF is not on the object distance Si, but has an offset $\Delta$(marked in FIG. 6), and in the image corner DOF, the resolutions of the images on the image sensing plane (at the image distance Si) when the image is at the object distance SiF and the image distance SiN are as high as possible and are approximate. In this way, as marked by circles with dotted line, the present embodiment has relatively great MTF in near object distance and far object distance imaging. The MTF for convention is relatively low, and thus the MTF value of the present embodiment is higher than the MTF value for convention, and the resolution of the corner region may be effectively promoted while maintaining the resolution of the image center region. Therefore, the design of the present invention may be optimized according to the foregoing state.

Figure 6:
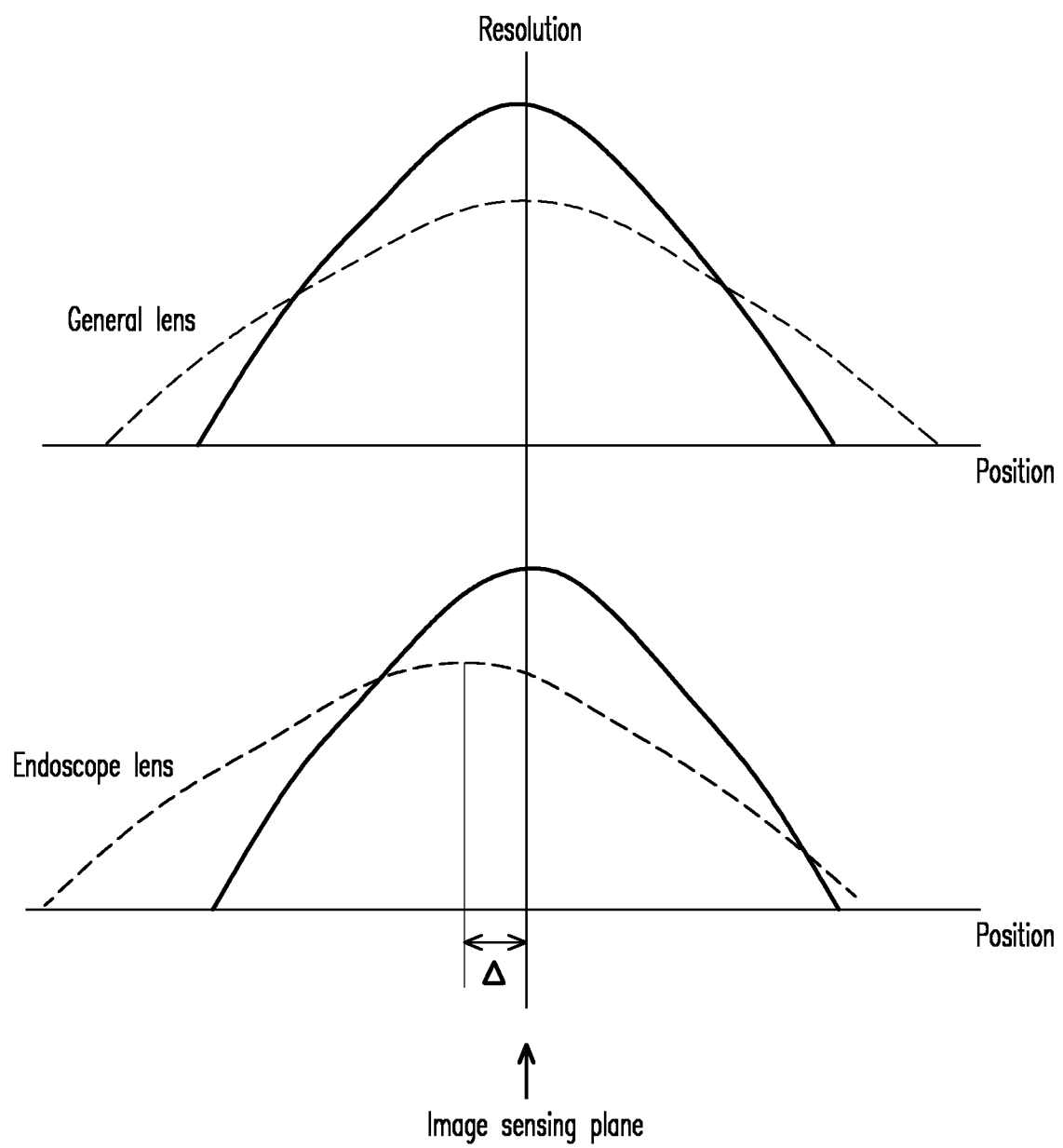
FIG. 6 shows MTF curve distribution of an embodiment of the present invention.

FIG. 6 shows that when the resolution shown in FIG. 5B is required to be achieved, with regard to the image corner DOF, the position (image distance) corresponding to the MTF peak is not on the image sensing plane (image distance Si), but shifts by an offset $\Delta$, and the offset $\Delta$ is toward the direction of image distance SiF. The solid line represents the curve of the center region, and the dotted line represents the curve of the corner region.

Figure 7:
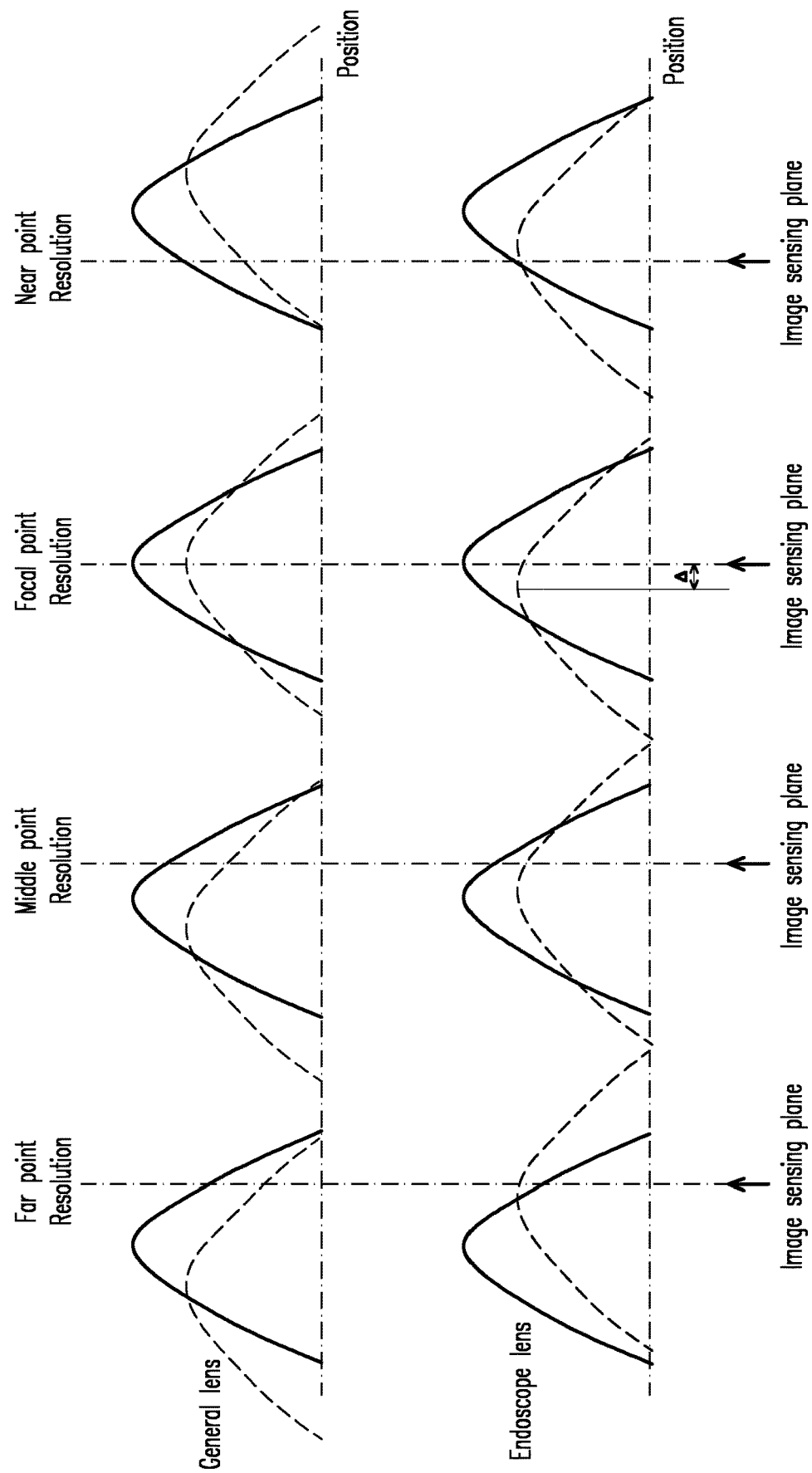
FIG. 7 shows a difference between the resolution MTF curve distribution of an embodiment of the present invention and the resolution MTF curve distribution of a general camera.

FIG. 7 shows a difference between the resolution MTF curve distribution of an embodiment of the present invention and the resolution MTF curve distribution of a general camera. The solid line represents the curve of the center region, and the dotted line represents the curve of the corner region. In the present embodiment, at the position of the focal point, the image distance corresponding to the peak of the resolution curve of the corner region shifts by a predetermined distance (offset $\Delta$) relative to the image distance corresponding to the peak of the resolution curve of the center region, and the position (image distance) corresponding to the MTF peak of the corner region is not on the image sensing plane (image distance Si). In the image corner DOF, the resolutions of the corner region at the far point, the middle point and the near point are as high as possible and are approximate at the image sensing plane.

Figure 8:
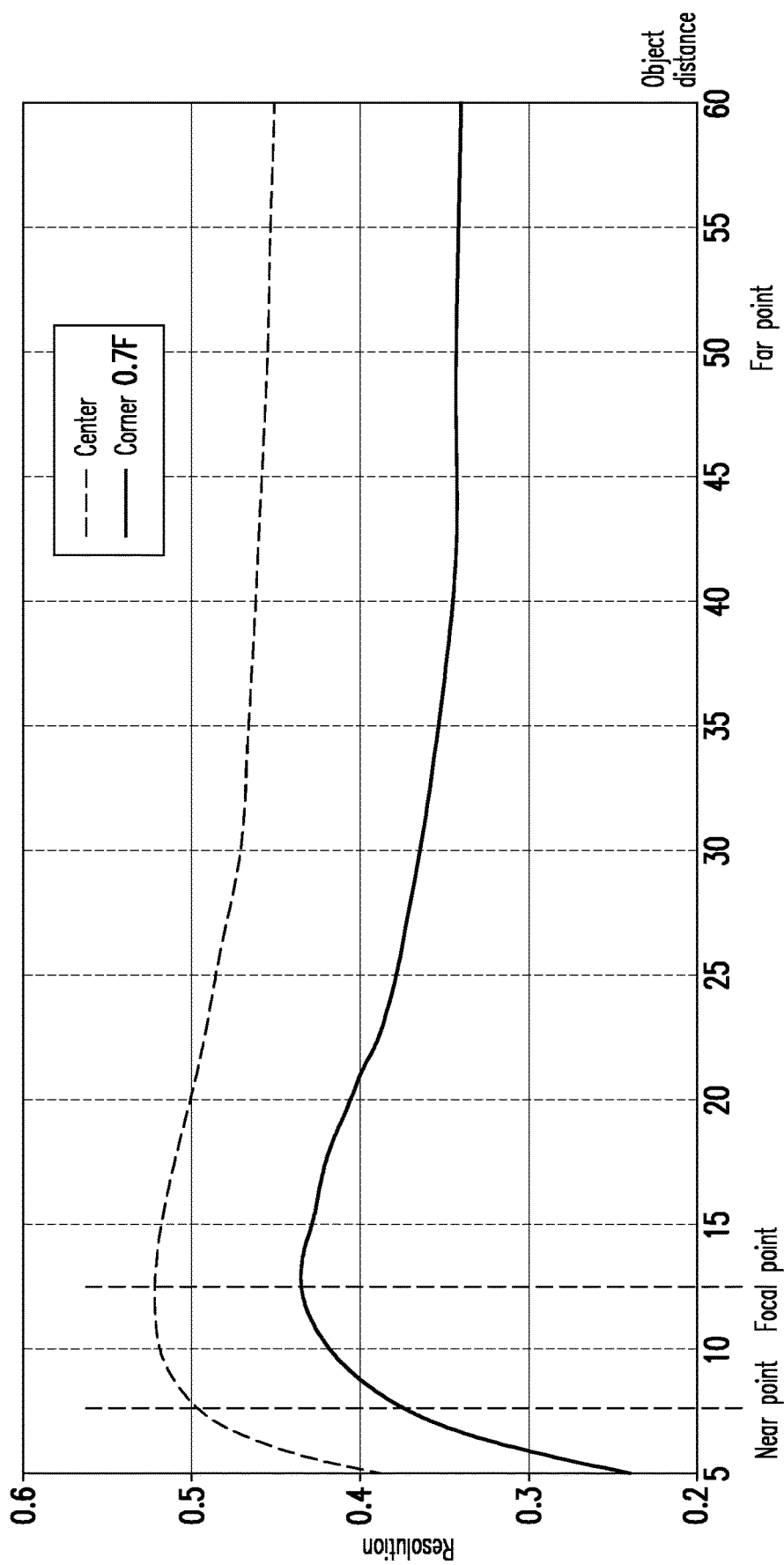
FIG. 8 shows variation of resolution of an existing general lens in a DOF range.

FIG. 8 shows variation of resolution of an existing general lens in a DOF range. The imaging distances of the corner region and the center region are the same, although the reduction margin of the corner resolution corresponding to the object distance at the far point is relatively small, the corner resolution corresponding to the object distance at the near point is low.

Figure 9:
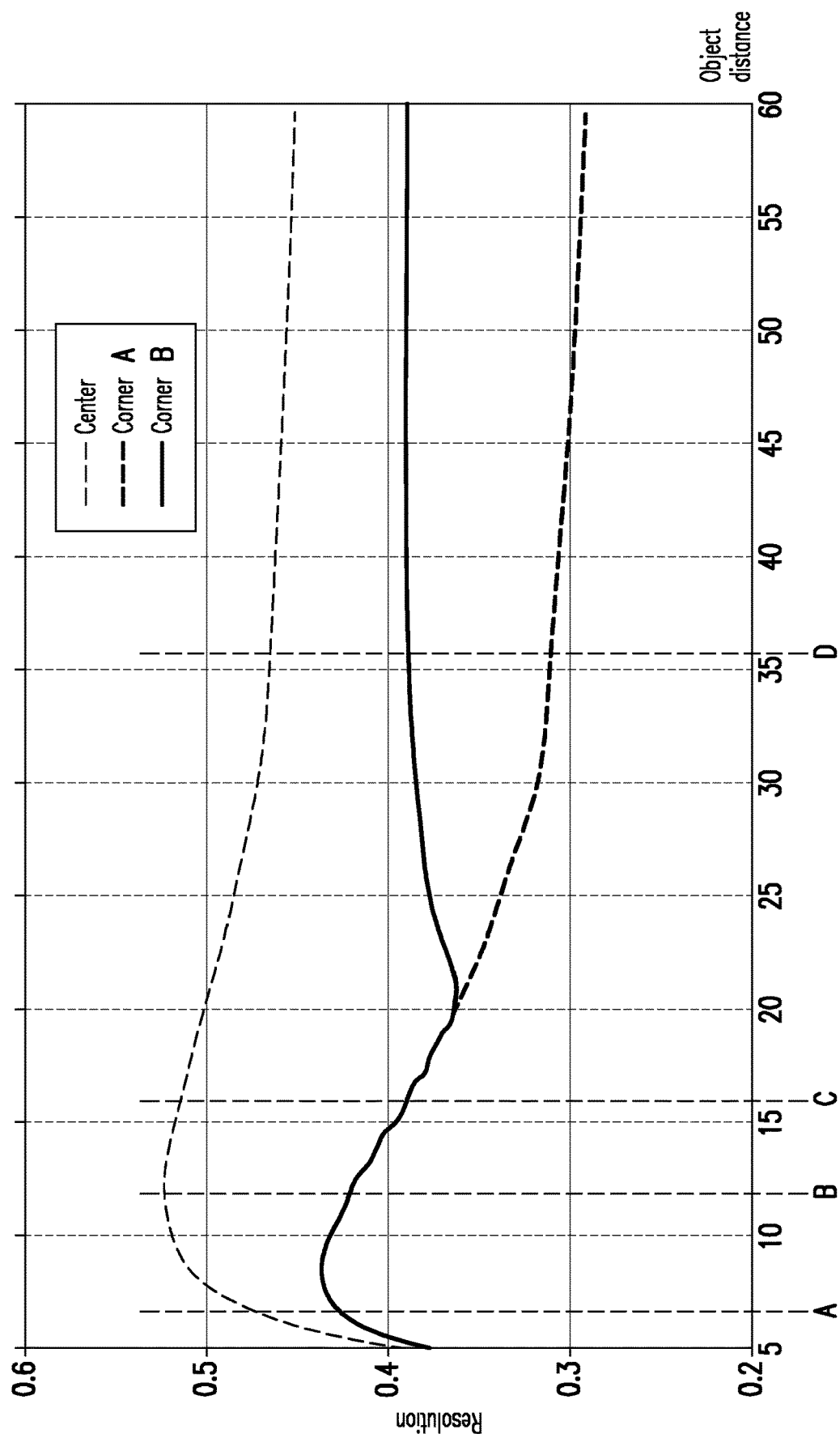
FIG. 9 shows variation of the resolution of the present embodiment in a DOF range.

FIG. 9 shows variations of the resolution of the present embodiment in the DOF range, and the MTF curves of the center field of view and the corner field of view (corner 0.7F). In the application of the endoscope of the present embodiment, by optimized adjustment, due to the offset $\Delta$, the resolution of the corner field of view of the near object distance is improved. The curve of the corner A represents a resolution curve corresponding to shooting of a general plane object, while the curve of the corner B represents the resolution curve corresponding to shooting of a non-planar plane. For the far object distance, if being used for shooting of a general plane object, the curve of the corner field of view is as shown by the curve of the corner A, and the MTF in a relatively far distance is gradually reduced. However, in the application of the endoscope of the present embodiment, what is shot is not a plane object, but corresponds to the corner object distance of the non-planar object, the resolution curve of the corner field of view is as shown by the curve of the corner B, and the resolution is obviously promoted. Similar curves may be formed according to such mode according to different shape distributions of the objects to which the endoscope is mainly applied, and the resolutions of the corner image at the near object distance and the far object distance will be both obviously promoted.

In the present embodiment, $\Delta/f$, for example, is between 1.5% and 10%, between 2% and 9% or between 2% and 7%, and A is image distance offset corresponding to the imaging resolution peak of the center region and the corner region, i.e., resolution peak offset, and f is the focal length.

The focal length f of the present embodiment, for example, is between 0.2 mm and 5 mm, a ratio of center farthest object distance/nearest object distance ranges between 2 and 200, and a ratio of the corner farthest object distance/nearest object distance ranges between 2 and 50.

Design of the entity of the optical lens may be performed according to the foregoing MTF curve, and because the foregoing MTF curve is entirely different from that of a conventional design mode, the endoscope lens with the MTF curve may achieve an effect that the imaging resolution of the object at the near point, the middle point and the far point distance is optimized, and therefore, the problems of the prior art are solved.

Therefore, the present invention provides a wide-angle endoscope lens, which is configure to capture a non-planar object to generate an image, wherein the ranges of depth of field respectively corresponding to a center region and a corner region of the image are different, the resolutions of a nearest object distance and a farthest object distance in the range of the depth of field of the center region are approximately equal, and the resolutions of a nearest object distance and a farthest object distance in the range of the depth of field of the corner region are substantially the same.

As for the lens of the endoscope with large angle of field of view, the corresponding object distance is taken as the imaging distance of the middle point object distance after an optimal design image distance is determined according to the imaging image distances of the object at the near point, the middle point and the far point of the center region in the range of depth of field. The set resolutions of the nearest point and the farthest point of the lens are almost equal. In such condition, the corner optimal imaging distance is adjusted to an extent that imaging of the corner region is in the object distance range of the object at the near point, the middle point and the far point, and the resolution is optimized; the optimization means that the overall resolution of the lens is relatively high in the range of depth of field, and the resolutions of the nearest point and the farthest point are approximately equal. Such endoscope lens reaches the optimization of the center and corner imaging resolutions in a special application environment of the endoscope.

The foregoing object distance is determined according to the object characteristics in the application field of the endoscope, however, as for the object surface of the present claim, the object of field of view in the range of depth of field does not approximate to a general shooting plane. According to the object characteristics, the object in the range of depth of field may be a non-planar object or an object varying continuously from the near point, the near-middle point, the middle point, the middle-far point to the far point.

The foregoing non-planar object may be a spherical surface, a cambered surface, a semi-ellipsoid surface, a paraboloid, a tubular surface or a barrel-shaped surface, and the object varying continuously has the object characteristic of gradually varying from plane, spherical surface or tubular surface, or gradually varying from other multiple surfaces, from the near point, the near-middle point, the middle point, the middle-far point to the far point.

The foregoing corner region means at least one field of view selected from a range between 0.5F (half field of view) and 1.0F (full field of view), for example, 0.5F, 0.7F, 0.85F or single field of view, or a combination of multiple fields of view. Moreover, the field of view may also be represented by using the image height of the image, or represented by using the angle of field of view, wherein the maximal image height, for example, corresponds to the maximal angle of field of view, and the object distance in the corner region refers to the distance of the object in the field of view of the corner region projected onto the optical axis.

The foregoing resolutions of the nearest point and the farthest point are substantially the same. The two may be the same by multiplying the resolutions of the nearest point and the farthest point by weighting parameters respectively, and the range of the weighting parameters is between 0.8 and 1.2. The weighting parameter ranges of the image center region and the image corner region are the same.

FIG. 10A and FIG. 10B are optical datas of the wide-angle endoscope lens of an embodiment of the present invention. FIG. 11A and FIG. 11B are optical datas of the wide-angle endoscope lens of another embodiment of the present invention. Referring to FIG. 10A and FIG. 10B as well as FIG. 11A and FIG. 11B, the wide-angle endoscope lens of the present embodiment sequentially includes a first lens, a second lens, an aperture, a third lens, a fourth lens and a fifth lens along the optical axis of the endoscope lens from the object side to the image side. Light emitted from a to-be-shoot object forms an image on an image plane after entering the endoscope lens and passing through the first lens, the second lens, the aperture, the third lens, the fourth lens and the fifth lens. The object side is the side facing the to-be-shoot object, while the image side is the side facing the image plane.

In the present embodiment, each of the first lens, the second lens, the third lens, the fourth lens and the fifth lens includes an object side surface facing the object side and an image side surface facing the image side, detailed optical datas of Embodiment 1 is as shown in FIG. 10A and FIG. 10B, and detailed optical datas of Embodiment 2 is as shown in FIG. 11A and FIG. 11B.

In Embodiment 1, the focal length f of the wide-angle endoscope lens is 0.431 mm, the shifted predetermined distance between the position (image distance) of the peak of the center resolution curve in the center object distance range and the position (image distance) of the peak of the corner resolution curve in the corner object distance range is 14 μm, a ratio of the predetermined distance to the focal length of the wide-angle endoscope lens is 3.2%, and the field of view of the wide-angle endoscope lens is 142 degrees.

Moreover, in Embodiment 1, the object side surfaces and the image side surfaces of the first lens, the second lens, the third lens, the fourth lens and the fifth lens may have at least one spherical surface and/or at least one aspheric surface, and the aspheric coefficients are as shown in FIG. 10B, where K is conic constant, and $a_2$, $a_4$, $a_6$, $a_8$ and $a_{10}$ are the $2i^{th}$ order of aspheric coefficients.

In Embodiment 2, the focal length f of the wide-angle endoscope lens is 0.586 mm, the shifted predetermined distance between the position (image distance) of the peak of the center resolution curve in the center object distance range and the position (image distance) of the peak of the corner resolution curve in the corner object distance range is 16 μm, a ratio of the predetermined distance to the focal length of the wide-angle endoscope lens is 2.7%, and the field of view of the wide-angle endoscope lens is 140 degrees.

Moreover, in Embodiment 2, the object side surfaces and the image side surfaces of the first lens, the second lens, the third lens, the fourth lens and the fifth lens may have at least one spherical surface and/or at least one aspheric surface, and the aspheric coefficients are as shown in FIG. 11B, where K is conic constant, and $a_2$, $a_4$, $a_6$, $a_8$ and $a_{10}$ are the $2i^{th}$ order of aspheric coefficients.

It should be noted that, Embodiment 1 and Embodiment 2 are illustrated by taking five lens as examples, however, in other embodiments, the wide-angle endoscope lens may have less than five or more than five lenses, and the present invention is not limited thereto. Moreover, Embodiment 1 and Embodiment 2 are illustrated by taking nine aspheric surfaces as examples respectively, however, in other embodiments, the wide-angle endoscope lens may have less than nine or more than nine aspheric surfaces, and the present invention is not limited thereto.

To sum up, in the wide-angle endoscope lens of the present invention, the image distance corresponding to the peak of the resolution curve of the corner region shifts by a predetermined distance relative to the image distance corresponding to the peak of the resolution curve of the center region, so that relatively high resolution is achieved in both near object distance imaging and far object distance imaging, and the resolution of the corner region may be effectively promoted while maintaining the resolution of the image center region.

Although the present invention has been disclosed above through the embodiments, the embodiments are not intended to limit the present invention, a person of ordinary skill in the art can make some alternation and modification without deviating from the spirit and scope of the present invention, and therefore, the protection scope of the present invention should be defined by the appended claims.

What is claimed is:

1. A wide-angle endoscope lens, configured to capture a large viewing angle area of a non-planar object to generate an image, wherein the wide-angle endoscope lens comprising:
    a center region, having a corresponding central object distance range; and
    a corner region, surrounding and adjoining the center region, and having a corresponding corner object distance range, wherein the central object distance range is different from the corner object distance range, a first resolution of the image of the non-planar object captured at a central shortest object distance in the central object distance range and a second resolution of the image of the non-planar object captured at a central farthest object distance in the central object distance range are substantially the same, and a third resolution of the image of the non-planar object captured at a corner shortest object distance in the corner object distance range and a fourth resolution of the image of the non-planar object captured at a corner farthest object distance in the corner object distance range are substantially the same.

2. The wide-angle endoscope lens according to claim 1, wherein a first ratio of the first resolution to the second resolution is between 0.8 and 1.2.

3. The wide-angle endoscope lens according to claim 1, wherein a first ratio of the first resolution to the second resolution is between 0.9 and 1.1.

4. The wide-angle endoscope lens according to claim 1, wherein a second ratio of the third resolution to the fourth resolution is between 0.8 and 1.2.

5. The wide-angle endoscope lens according to claim 1, wherein a second ratio of the third resolution to the fourth resolution is between 0.9 and 1.1.

6. The wide-angle endoscope lens according to claim 1, wherein a proportion of the corner farthest object distance to the corner shortest object distance ranges between 2 and 50.

7. The wide-angle endoscope lens according to claim 1, wherein a position of an image distance corresponding to a peak of a central resolution curve in the central object distance range shifts by a predetermined distance from a position of an image distance corresponding to the peak of a corner resolution curve in the corner object distance range.

8. The wide-angle endoscope lens according to claim 7, wherein a ratio of the predetermined distance to a focal length of the wide-angle endoscope lens is between 1.5% and 10%.

9. The wide-angle endoscope lens according to claim 1, wherein the non-planar object has one selected from a group consisting of a spherical surface, a cambered surface, a semi-ellipsoid surface, a paraboloid, a tubular surface and a barrel-shaped surface.

10. The wide-angle endoscope lens according to claim 1, wherein the wide-angle endoscope lens has one field of view, the corner region is located between N fields of view and 1.0 field of angle, and N is a decimal between 0.5 and 1.0.

11. The wide-angle endoscope lens according to claim 10, wherein N is a decimal between 0.6 and 0.8.

12. The wide-angle endoscope lens according to claim 1, wherein the wide-angle endoscope lens has an angle of field of view which is greater than or equal to 110 degrees.

13. A wide-angle endoscope lens, configured to capture a large viewing angle area of a non-planar object to generate an image, wherein the wide-angle endoscope lens comprising:
    a center region; and
    a corner region, surrounding and adjoining the center region, wherein a position of an image distance corresponding to a peak of a resolution curve in the corner region of the wide-angle endoscope lens shifts by a predetermined distance relative to a position of an image distance corresponding to a peak of a resolution curve in the center region.

14. The wide-angle endoscope lens according to claim 13, wherein a ratio of the predetermined distance to a focal length of the wide-angle endoscope lens is between 1.5% and 10%.

15. The wide-angle endoscope lens according to claim 13, wherein the center region has a corresponding central object distance range, the corner region has a corresponding corner object distance range, and the central object distance range is different from the corner object distance range.

16. The wide-angle endoscope lens according to claim 13, wherein the wide-angle endoscope lens comprises a plurality of lenses, and at least one surface of the plurality of the lenses is an aspheric surface.

17. The wide-angle endoscope lens according to claim 13, wherein the wide-angle endoscope lens comprises a plurality of lenses, and at least one surface of the plurality of the lenses is a spherical surface.

18. The wide-angle endoscope lens according to claim 13, wherein the position of the image distance corresponding to the peak of the resolution curve in the corner region of the wide-angle endoscope lens shifts from an image sensing plane.

* * * * *